US008568753B2

(12) United States Patent
Grogan et al.

(10) Patent No.: US 8,568,753 B2
(45) Date of Patent: Oct. 29, 2013

(54) DELIVERY SYSTEM

(75) Inventors: Owen Timothy Grogan, Black Rock (AU); Thomas David McCarthy, Malvern East (AU)

(73) Assignee: Starpharma Pty Limited, Melbourne, Victoria (AU)

( * ) Notice: Subject to any disclaimer, the term of this patent is extended or adjusted under 35 U.S.C. 154(b) by 807 days.

(21) Appl. No.: 12/090,580

(22) PCT Filed: Feb. 1, 2006

(86) PCT No.: PCT/AU2006/000120
§ 371 (c)(1),
(2), (4) Date: Mar. 3, 2010

(87) PCT Pub. No.: WO2007/045009
PCT Pub. Date: Apr. 26, 2007

(65) Prior Publication Data
US 2010/0252050 A1    Oct. 7, 2010

(30) Foreign Application Priority Data

Oct. 18, 2005  (AU) ................... 2005905750

(51) Int. Cl.
| A01N 25/10 | (2006.01) |
| A01N 41/04 | (2006.01) |
| A61F 6/04  | (2006.01) |
| A61F 6/06  | (2006.01) |
| A61K 31/785 | (2006.01) |

(52) U.S. Cl.
USPC ......... 424/404; 128/830; 128/832; 128/841; 128/844; 424/407; 424/411; 424/422; 424/430; 424/DIG. 16; 424/78.07; 424/78.37; 514/550; 514/568; 514/709; 523/122

(58) Field of Classification Search
USPC .................................. 514/550, 568, 709
See application file for complete search history.

(56) References Cited

U.S. PATENT DOCUMENTS

| 5,229,490 A |   | 7/1993  | Tam |
| 5,985,275 A | * | 11/1999 | Neurath et al. ............ 424/133.1 |
| 6,464,971 B1 | * | 10/2002 | Matthews et al. .......... 424/78.17 |

FOREIGN PATENT DOCUMENTS

| JP | 9512264 A    | 12/1997 |
| JP | 2004515457 A | 5/2004  |
| JP | 2005532276 A | 10/2005 |
| WO |    95/28966 A1  | 11/1995 |
| WO | WO 95/34595 A   | 12/1995 |
| WO | WO 00/15239 A   | 3/2000  |
| WO | WO 00/15240 A   | 3/2000  |
| WO |    01/87348 A2  | 11/2001 |
| WO | WO 02/15832 A1  | 2/2002  |
| WO | WO 02/79298 A1  | 10/2002 |
| WO | WO 02/079299   * | 10/2002 |
| WO | WO 02/079299 A1 | 10/2002 |
| WO |    03/076455 A2 | 9/2003  |

OTHER PUBLICATIONS

Bourne, N. et al. 2000 Dendrimers, a New Class of Candidate Topical Microbicides with Activity against Herpes Simplex Virus Infection *Antimicrobial Agents and Chemotherapy* 44(9):2471-2474.
Liu, et al., Water Soluble Dendrimer-Poly(ethylene glycol) Starlike Conjugates as Potential Drug Carriers, Journal of Polymer Science Part A: Polymer Chemistry, vol. 37, Mar. 25, 1999, pp. 3492-3503.
Telwatte et al. "Virucidal activity of the dendrimer microbicide SPL7013 against HIV-1", Antiviral Research, 90: 195-199 (2011).
Tyssen et al. "Structure activity relationship of dendrimer microbicides with dual action antiviral activity", PLosOne, vol. 5, Issue 8: e12309 (1-15) (Aug. 2010).
Wyand et al. "Effect of 3-hydroxyphthaloyl-beta-lactoglobulin on vaginal transmission of simian immunodeficiency virus in Rhesus Monkeys", Antimicrobial Agents and Chemotherapy, vol. 43, No. 4: 978-980 (Apr. 1999).
Price et al. "SPL7013 Gel (VivaGel) retains potent HIV-1 and HSV-2 inhibitory activity following vaginal administration in humans", PLosOne, vol. 6, issue 9: e24095 (1-12) (Sep. 2011).
Extended European Search Report for European Application No. 06704802.5, dated Nov. 15, 2012.
Bernstein et al., "Evaluations of Unformulated and Formulated Dendrimer-Based Microbicide Candidates in Mouse and Guinea Pig Models of Genital Herpes", Antimicrobial Agents and Chemotherapy, American Society for Microbiology, vol. 47, No. 12, Dec. 2003, pp. 3784-3788.
McCarthy et al., "Dendrimers as Drugs: Discovery and Preclinical and Clinical Development of Dendrimer-Based Microbicides for HIV and STI Prevention", Molecular Pharmaceutics, American Chemical Society, vol. 2, No. 4, Jul. 2005, pp. 312-328.
Tuprin, "Considerations and development of topical microbicides to inhibit the sexual transmission of HIV", Expert Opinion on Investigational Drugs, Ashley Publications Ltd., vol. 11, No. 8, Jan. 2002, pp. 1077-1097.

\* cited by examiner

*Primary Examiner* — Neil Levy
(74) *Attorney, Agent, or Firm* — Knobbe, Martens, Olson & Bear, LLP

(57) ABSTRACT

A microbicidal delivery system including: a microbicidal composition including a microbicidal compound including a dendrimer including one or more surface groups of formula (IV); a microbicidally active derivative thereof, or pharmaceutically acceptable salt or solvate thereof; and a carrier, excipient or diluent therefor; and a prophylactic device; the microbicidal composition being carried on a surface of the prophylactic device and being compatible therewith.

17 Claims, No Drawings

DELIVERY SYSTEM

This application is U.S. National Phase of International Application PCT/AU2006/000120, filed Feb. 1, 2006 designating the U.S., and published in English as WO 2007/045009 on Apr. 26, 2007, which claims priority to Australian Patent Application No. 2005905750, filed Oct. 18, 2005.

The present invention relates to the prevention and treatment of sexually transmitted infections and, in particular, relates to the use of a condom carrying a dendrimer having naphthyl disulfonate terminal groups.

The global incidence of morbidity and mortality of sexually transmitted infections (STIs) caused by Human Immunodeficiency virus (HIV), Herpes virus (HSV) and other viral and microbial pathogens is estimated at several hundred million individuals worldwide. One approach to control the transmission of STIs is the use of topically applied, female/male controlled vaginal or rectal microbicides that inactivate the relevant pathogens.

It has further been found that the use of detergent-based microbicides such as nonoxynol-9 (N-9) may have adverse effects in the prevention of HSV-2 or HIV. Whilst such detergents act by disrupting HSV and HIV membranes, they may also compromise the natural vaginal barrier and significantly increase susceptibility to infection.

International patent application no PCT/AU02/00407 (WO 02/079299), to applicants, the contents of which are incorporated herein by reference, discloses a class of dendrimers, (highly branched macromolecules with a definite envelope of polyanionic or cationic surface groups) which have been shown to exhibit a range of antiviral and antimicrobial activity with minimal toxicity.

In antiviral and antimicrobial testing, a subset of these dendrimer structures have unexpectedly shown exceptional activity against a broad spectrum of microorganisms associated with sexually transmitted infection that makes them agents of choice for the development of a vaginal or rectal microbicide for the treatment or prophylaxis of sexually transmitted infections.

One compound in particular, SPL7013, formula I,

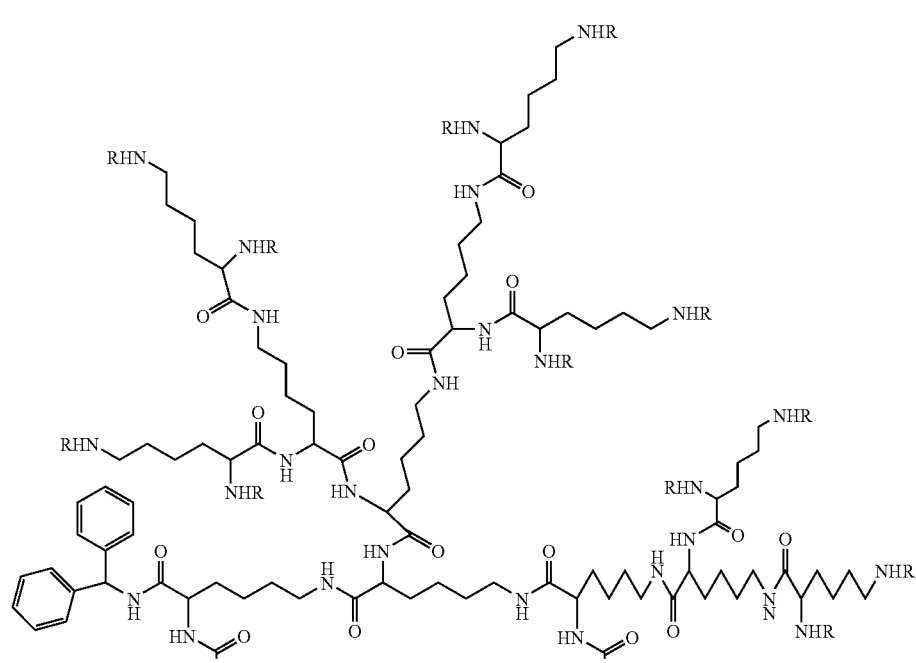

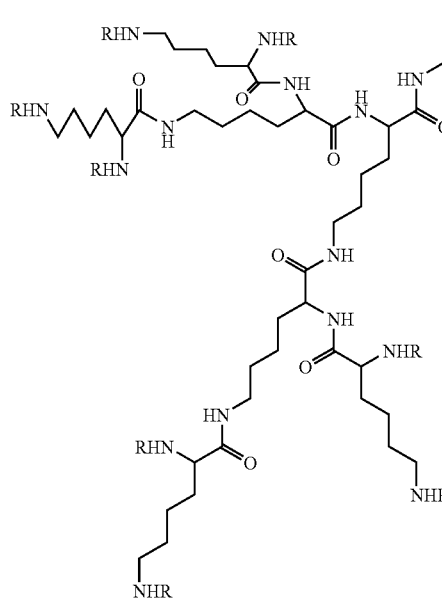
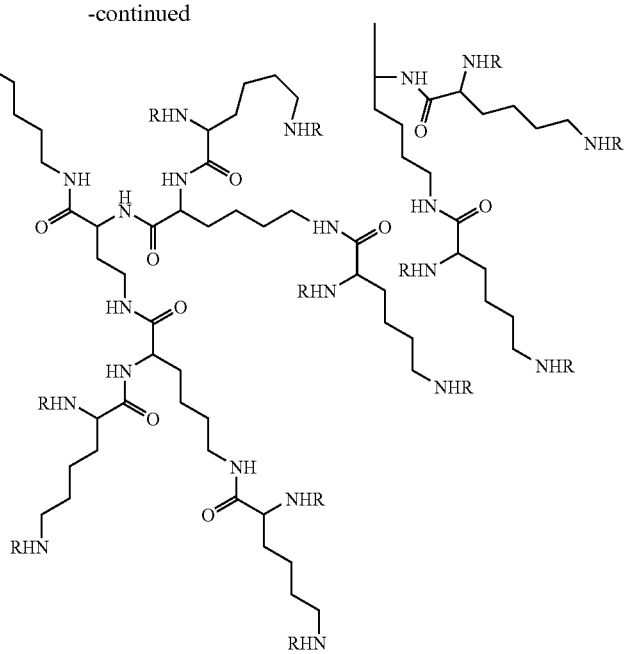

where R represents a group of the formula IV

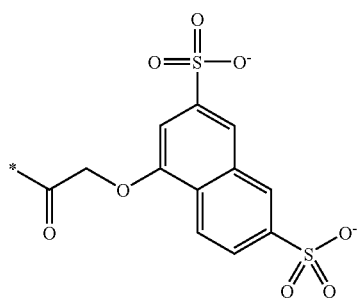

IV or a pharmaceutically acceptable salt or solvate thereof; for example, has been found to have activity against various sexually transmitted infections.

SPL7013 consists of a polylysine dendrimer scaffold with the active surface groups consisting of 32 naphthyl disulphonic acid groups. Each of the naphthyl disulphonate surface groups is attached to the branched dendrimer scaffold with an amido-methyleneoxy linkage to the 32 terminal groups.

There are a number of options for the administration of the type of compound represented, for example, by formula I or a pharmaceutically acceptable salt or solvate thereof, in the treatment or prophylaxis of sexually transmitted infections, for example topical administration. A variety of topical administration routes are available. The particular mode selected will depend, of course, upon the particular condition being treated and the dosage required for preventative efficacy. Such modes of administration include the vaginal, rectal, oral and trans-dermal routes. Suitable formulations for topical, particularly vaginal or rectal, administration include solutions, suspensions, gels, lotions, foams, films, jellies, and creams as well as discrete units such as suppositories and microencapsulated suspensions. Other delivery systems can include sustained release delivery systems which can provide for slow release of the active component of the invention, including sustained release gels, creams, suppositories, or capsules.

However, some of the topical modes of administration may have some disadvantages. For example, vaginal or rectal suppositories may not provide medication to the entire vagina or rectum due to their shape and/or placement in the vagina or rectum by the user. In addition, the medication being supplied by the suppositories may drain out of the vagina or rectum rather quickly, thus reducing the potential effectiveness of the medication. Similarly, the application of topical formulations in the form of a foam, jelly, cream or film may be messy, and the effectiveness of the formulation may be reduced due to drainage of the formulation from the vagina or rectum.

Barrier methods, for example, condoms, are also used to prevent sexually transmitted infections. However, condoms have been known to rupture due to stresses, caused by, for example, stretching or incorrect use. Condoms may also develop microscopic leaks, or may contain small perforations that may lead to transfer of bodily fluids across the barrier, leading to risk of infection.

It is, accordingly, an object of the present invention to overcome or at least alleviate one or more of the difficulties and deficiencies related to the prior art.

SUMMARY OF THE INVENTION

In a first embodiment of the present invention, there is provided a microbicidal delivery system including:
  a microbicidal composition including
    a microbicidal compound including a dendrimer including one or more surface groups of formula IV

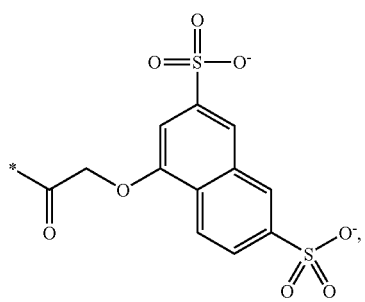

IV a microbicidally active derivative thereof, or pharmaceutically acceptable salt or solvate thereof; and
a carrier, excipient or diluent therefor; and
a prophylactic device;
the microbicidal composition being carried on a surface of the prophylactic device and being compatible therewith.

DETAILED DESCRIPTION OF THE INVENTION

As used herein in this specification and claims, the singular forms "a", "an" and "the" include plural referents unless the context clearly dictates otherwise. Thus, for example, reference to a "a macromolecule" includes one or more such macromolecules.

By the term "comprises" (or its grammatical variants) as used herein in this specification and claims is equivalent to the term "includes" and should not be taken as excluding the presence of other elements or features.

By the term "surface of the prophylactic device" as used herein in the specification and claims, we mean either the internal surface or the external surface or both surfaces of the device.

It has surprisingly been found that the efficacy of the microbicidal composition may be increased by delivery of the composition to the potential site(s) of infection concomitant with sexual activity.

Further, the potential adverse consequences of the partial failure of the prophylactic device may be substantially reduced with the inclusion of the microbicidal composition, as described above.

The delivery system according to this aspect of the present invention may also reduce or eliminate the adverse side effects associated with detergent-based microbicides, resulting in significantly decreased susceptibility to infection with HSV-2 or HIV.

Preferably, the microbicidal compound is selected from one or more of SPL7013 (represented by formula I below), SPL7304 (represented by formula II below), SPL7320 (represented by formula III below), where R in each case is represented by the group of formula IV; a microbicidally active derivative thereof, and a pharmaceutically acceptable salt or solvate thereof.

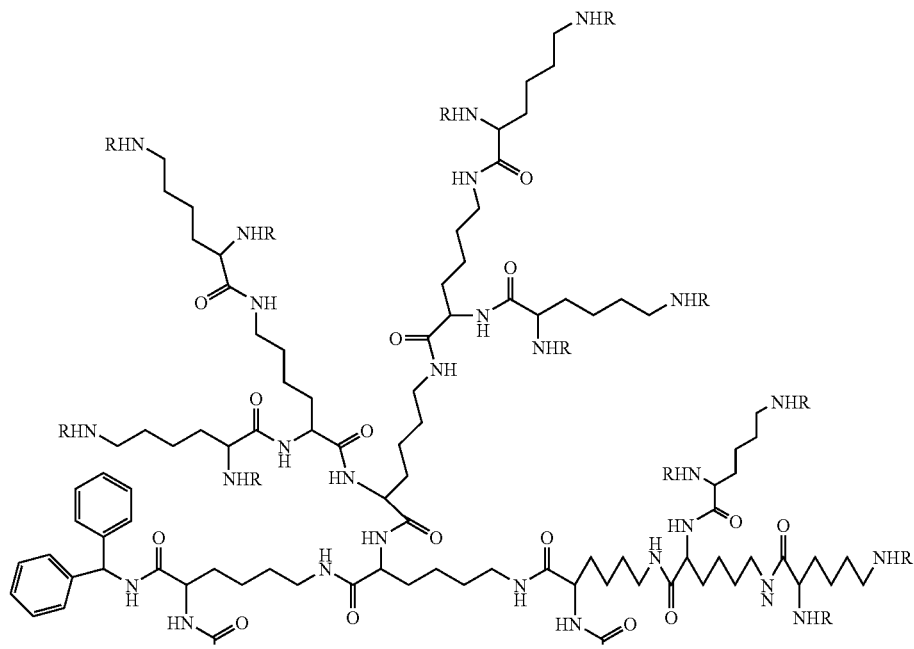

I 7 8
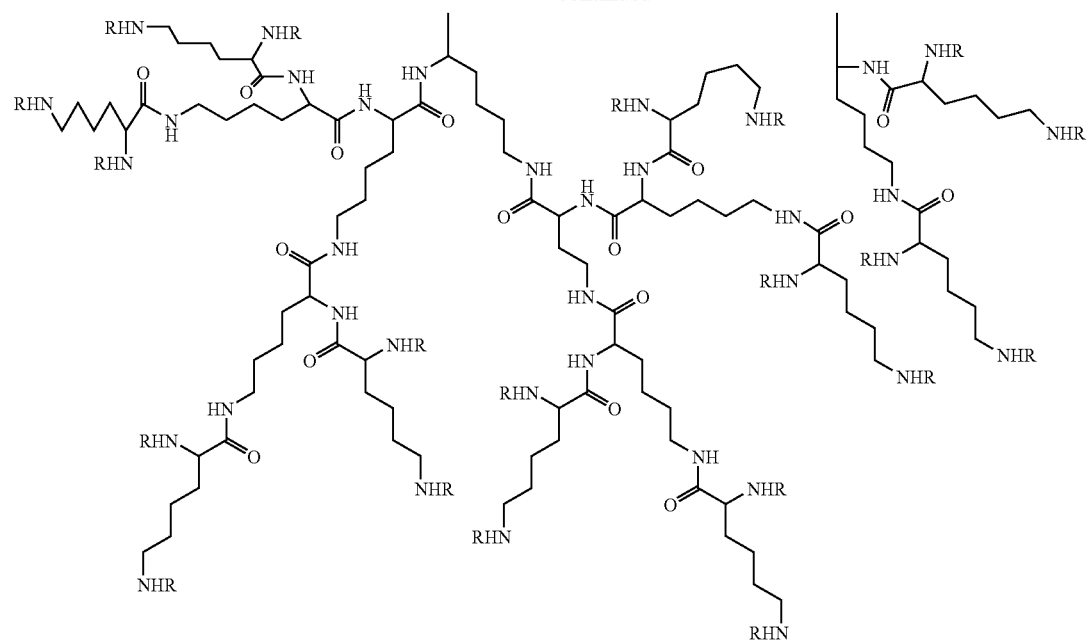
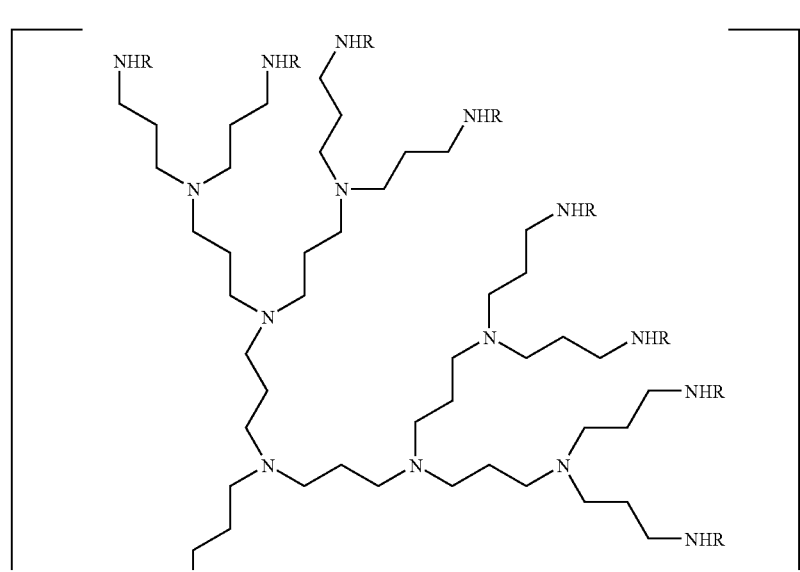

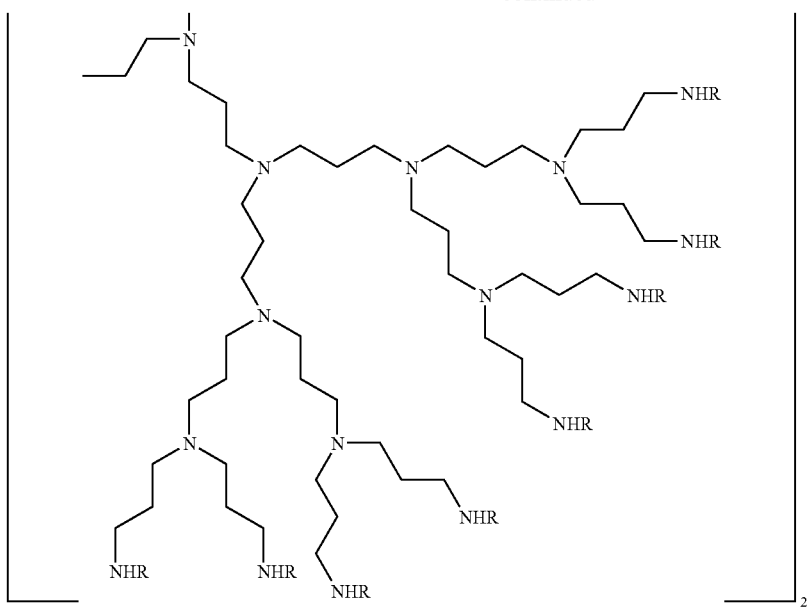
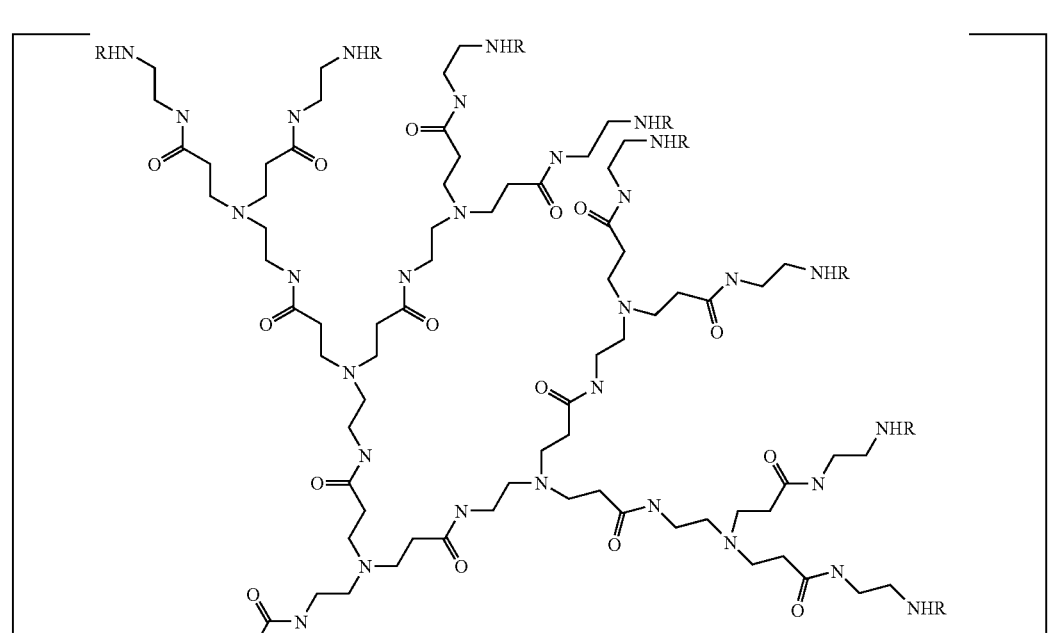

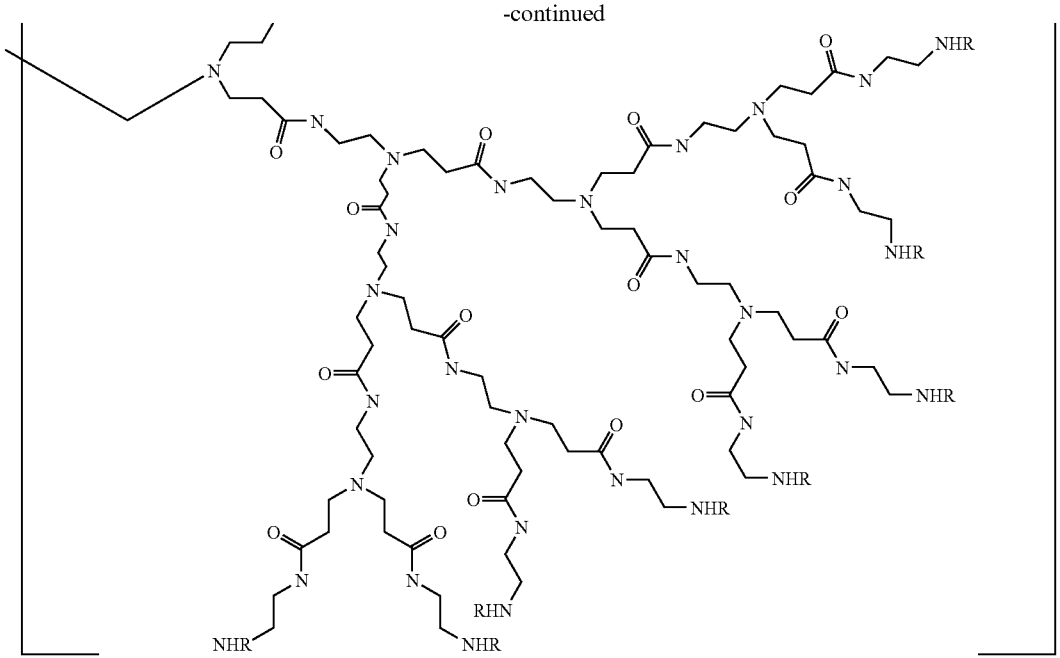

where R represents a group of the formula IV

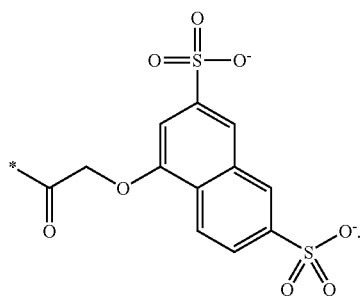

IV

The structures of these compounds consist of a polylysine dendrimer, a polypropyleneimine dendrimer, and a polyamidoamine (PAMAM) dendrimer scaffold respectively, with the active surface groups consisting of 32 naphthyl disulphonic acid groups as sodium salts. Each of the naphthyl-disulphonate functional surface groups is attached to the branched dendrimer scaffold with an amido-methyleneoxy linkage to the 32 terminal groups. The compound SPL7013 is preferred.

As described above, the compounds SPL7013, SPL7304, and SPL7320 are preferred compounds of the present invention, and have been found to exhibit significant antiviral activity, particularly against viral and microbial vectors of the most common sexually transmitted infections. Common sexually transmitted infections include, but are not limited to papillomaviruses, Chlamydia trachomatis, Candida albicans, Trichomonas vaginalis, Herpes simplex viruses, Cyclomegalovirus, Neisseria gonorrhoeae, Human Immunodeficiency viruses, Treponema pallidum, Hepatitis B and C viruses, Calymmato bacterium granulomatis, Haemophilus ducreyi, Sarcoptes scabiei, Phthirus pubis, Mycoplasma, Gardnerella vaginalis.

SPL7013 exhibits a broad-spectrum antiviral activity with high efficacy and minimal cell or animal toxicity, against vectors of several of the most important vaginally or rectally sexually transmitted infections. High activity has been determined against genital Herpes virus-2 (HSV-2) both in vitro cell tests and in vivo in an animal (mouse) model test and in vitro cell tests against Herpes virus-1 (HSV-1) and Human Immunodeficiency viruses (HIV-1 and HIV-2). It has also been shown to be active against the causative agent of genital warts, Human Papillomavirus (HPV), and against the bacterial vector of non-specific urethritis, Chlamydia trachomatis. In cell tests, SPL7013 has also shown activity against viral strains of Herpes virus-2 that are resistant to currently used modified nucleoside based antiviral agents. In addition SPL7304 and SPL7320 show high activity against HSV-1, HSV-2, HIV-1, and HIV-2. Furthermore SPL7013, SPL7304 and SPL7320 are active in CD4-dependant and CD4-independent HIV transmission assays, and are effective at preventing HIV-1 attachment and fusion. All compounds have been shown not to inhibit the growth of various species of beneficial Lactobacillus. In addition SPL7013, SPL7304, and SPL7320 have been shown to be effective in the prevention of infection of human peripheral blood monocular cells (PBMCs) with either HIV-1 RoJo or SIV 89. 6pd.

The pharmaceutically acceptable salt or solvate may be of any suitable type. Examples of suitable salts include, but are not limited to metallic salts (for example, aluminium, calcium, lithium, magnesium, potassium, sodium and zinc salts), organic salts (for example, N,N$'$-dibenzylethylenediamine, chloroprocaine, diethanolamine, ethylenediamine, cyclohexylamine, meglumine, (N-methylglucamine) and procaine), quaternary amines (for example, choline), sulphonium salts and phosphonium salts.

The microbicidal composition preferably has a viscosity such that it remains in contact with the prophylactic device for an extended period of time, and does not flow off the prophylactic device on contact.

As stated above, the microbicidal composition of this embodiment of the present invention includes a carrier, excipient or diluent. The microbicidal composition may be provided in the form of a solution, suspension, lotion, film, jelly, foam, gel, cream and the like. The carrier, excipient or diluent may include one or more of any and all conventional solvents, dispersion media, fillers, solid carriers, aqueous solutions, coatings, viscosity modifying agents, antibacterial and anti fungal agents, isotonic, and absorption enhancing or delaying agents, activity enhancing or delaying agents and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional carrier and/or diluent is incompatible with the active ingredient, use thereof in the microbicidal compositions of the present invention is contemplated.

Vehicles suitable for topical administration include oil-in-water and water-in-oil emulsions, white petrolatum, hydrophilic petrolatum, lanolin emulsions, polyethylene glycols, cocoa butter, buffering agents (including Carbopol 971P), emollient oils (e.g. water-soluble oils including, for example, polyethylene glycol), a lubricating gel (including, for example, water, propylene glycol, hydroxyethyl cellulose, benzoic acid and sodium hydroxide), a water-soluble oil (including, for example, glycerine, propylene glycol, polyquaternium #5, methyl paraben and propyl paraben), a cream (including, for example, benzyl alcohol, cetearyl alcohol, cetyl esters, wax, octyldodecanol, polysorbate 60, purified water, and sorbitan monostearate), and the like.

Preferably, the carriers, excipients and/or diluents include one or more of the group consisting of sodium hydroxide, water soluble oils, buffering agents, propylene glycol, glycerine and water. More preferably, the carriers, excipients and/or diluents include sodium hydroxide, edetate disodium dihydrate, methyl paraben, propyl paraben, Carbopol 971P, propylene glycol, glycerine, and purified water in combination.

The microbicidal composition may further include a secondary pharmaceutically active compound.

Accordingly, in a further embodiment of the present invention there is provided a microbicidal composition including
a microbicidal compound including a dendrimer including one or more surface groups of the formula IV

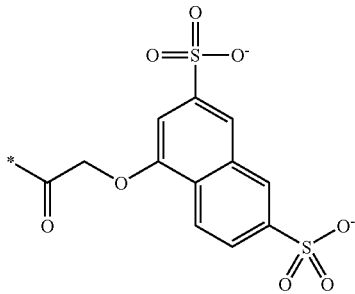

IV a microbicidally active derivative thereof, or pharmaceutically acceptable salt or solvate thereof;
a secondary pharmaceutically active compound; and
a carrier, excipient or diluent therefor.

The secondary pharmaceutically active component may be exemplified by, but not limited to, one or more of the compounds selected from the group consisting of:

| Acetonemia preparations | Anabolic agents |
| --- | --- |
| Anaesthetics | Analgesics |
| Anti-acid agents | Anti-arthritic agents |
| Antibacterials | Antibodies |
| Anti-convulsivants | Anti-fungals |
| Anti-histamines | Anti-infectives |
| Anti-inflammatories | Anti-microbials |
| Anti-parasitic agents | Anti-protozoals |
| Anti-STI agent | Anti-ulcer agents |
| Antiviral pharmaceuticals | Behaviour modification drugs |
| Biologicals | Blood and blood substitutes |
| Bronchodilators and expectorants | Cancer therapy and related pharmaceuticals |
| Cardiovascular pharmaceuticals | Central nervous system pharmaceuticals |
| Contrast agents | Contraceptives |
| Diabetes therapies | Diuretics |
| Fertility pharmaceuticals | Growth hormones |
| Growth promoters | Hematinics |
| Hemostatics | Hormones and analogs |
| Hormone replacement therapies | Immunostimulants |
| Minerals | Muscle relaxants |
| Natural products | Nutraceuticals and nutritionals |
| Obesity therapeutics | Ophthalmic pharmaceuticals |
| Osteoporosis drugs | Pain therapeutics |
| Peptides and polypeptides | Respiratory pharmaceuticals |
| Sedatives and tranquilizers | Transplantation products |
| Urinary acidifiers | Vaccines and adjuvants |
| Vitamins | |

Preferably, the secondary pharmaceutically active compound is a contraceptive or an agent active against sexually transmitted infections. More preferably, the secondary pharmaceutically active compound is a contraceptive, most preferably, a spermicide. Examples of contraceptives and agents active against sexually transmitted infections include, but are not limited to, podophyllin, tetracycline, nyastatin, fluconazole, metronidazole, acyclovir, penicillin, cefotaxime, spectinomycin, retrovir, erythromycin, ceftriaxone, cotrimoxazole, benzyl benzoate, malathion, nonoxynol-9, octoxynol-9, menfegol, progestin, estrogen, and estradiol. Other suitable secondary pharmaceutically active components which are contraceptives or agents active against sexually transmitted infections would be known to the person skilled in the art.

The microbicidal composition may be carried on the prophylactic device in any suitable manner. Examples include, but are not limited to, the composition being carried on a surface of the prophylactic device (for example, the internal surface, the external surface or both surfaces of the device), impregnated into the prophylactic device, covalently bound to a surface of the prophylactic device, and the like.

The prophylactic device may be of any suitable type. a condom, a cervical cap, contraceptive diaphragm, vaginal sponge, pessary, or the like may be used. A condom is preferred.

The prophylactic device and microbicidal composition may be selected to ensure compatibility there between.

Where a condom is used as the prophylactic device, the microbicidal composition may be carried on an external surface and/or an internal surface of the condom. Preferably, the microbicidal composition covers at least a substantial portion of the external surface and/or the internal surface of the condom.

In a preferred aspect of this embodiment of the present invention, there is provided a microbicidal delivery system including
a microbicidal compound of formula I
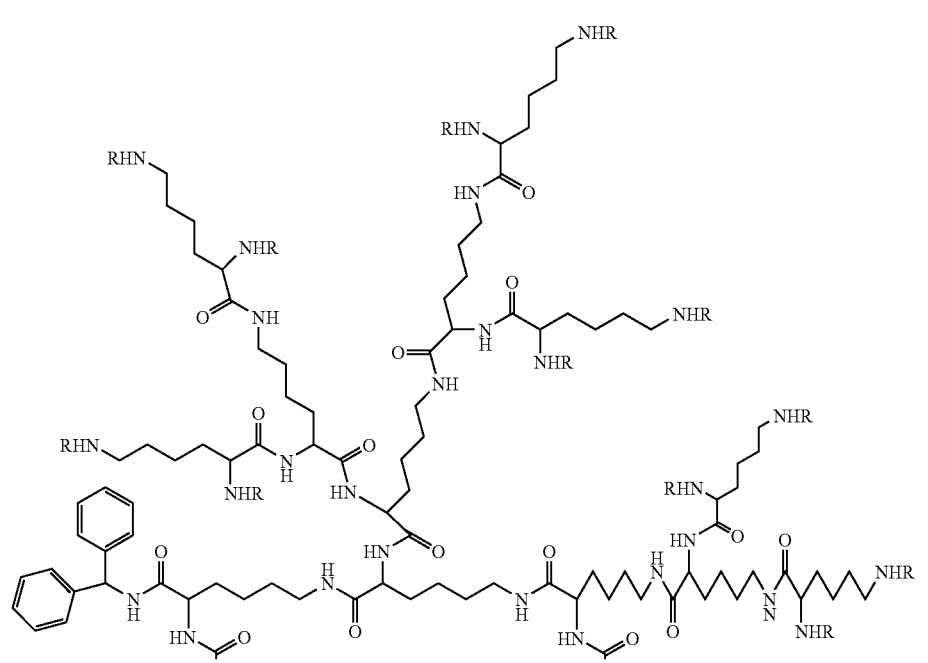
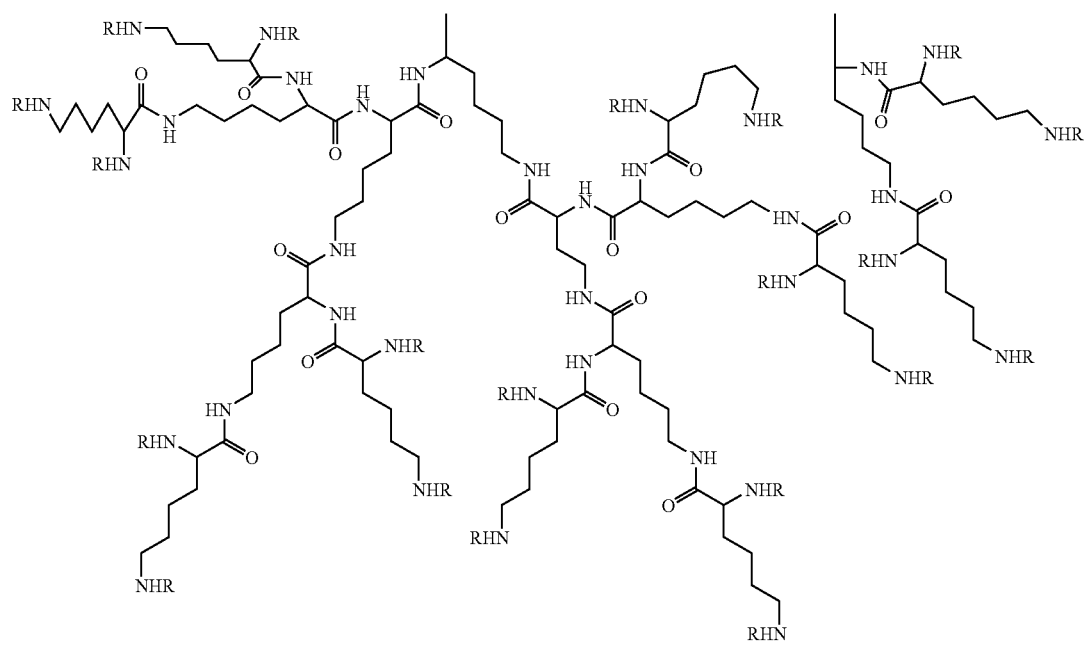

where R represents a group of the formula IV

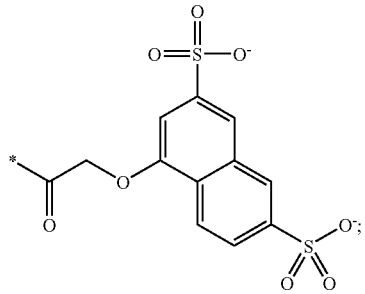

a carrier, excipient or diluent therefor; and
a condom;
the microbicidal composition being carried on a surface of the condom and being compatible therewith.

In a further embodiment of the present invention, there is provided a microbicidal delivery system including
a microbicidal composition including
a microbicidal compound including a dendrimer including one or more surface groups of formula IV

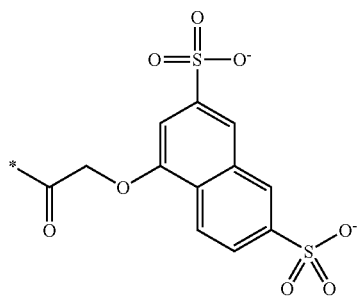

a microbicidally active derivative thereof, or pharmaceutically acceptable salt or solvate thereof;
a secondary pharmaceutically active compound; and
a carrier, excipient or diluent therefor; and
a prophylactic device;
the microbicidal composition being carried on a surface of the prophylactic device and being compatible therewith.

Preferably the secondary pharmaceutically active compound is an agent active against sexually transmitted infections.

In another embodiment of the present invention, there is provided a method for the prevention of sexually transmitted infections in a human patient, including providing a microbicidal delivery system, including:
a microbicidal composition including
a microbicidal compound including a dendrimer including one or more surface groups of formula IV

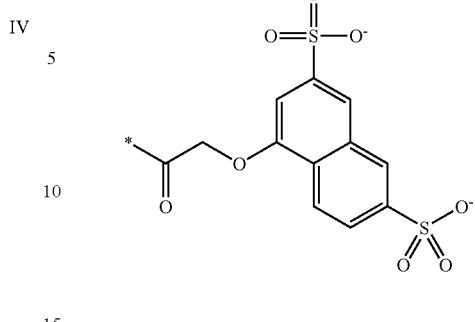

a microbicidally active derivative thereof, or
a pharmaceutically acceptable salt or solvate thereof; and
a carrier, excipient or diluent therefor; and
a prophylactic device;
the microbicidal composition being carried on a surface of the prophylactic device and being compatible therewith.

The microbicidal compound may be present in any suitable amounts. The amount of microbicidal composition should be sufficient for the reduction or prevention of sexually transmitted infections. This amount may depend on the particular sexually transmitted infection sought to be prevented, and individual patient parameters including age, physical condition, size, weight and concurrent treatment(s). These factors are well known to those of ordinary skill in the art and can be addressed with no more than routine experimentation.

The weight % of microbicidal compound included in the microbicidal composition according to the present invention may be in the range of about 0.5% to 20% weight/weight, more preferably in the range of about 1% to 18% weight/weight, most preferably in the range of about 2% to 15% weight/weight.

The microbicidal composition according to the present invention may be administered in an amount sufficient for the prevention of sexually transmitted infections. This amount may depend on the particular sexually transmitted infection sought to be prevented, and individual patient parameters including age, physical condition, size, weight and concurrent treatment(s). These factors are well known to those of ordinary skill in the art and can be addressed with no more than routine experimentation.

The amount of microbicidal composition included in the microbicidal delivery system according to the present invention may be in the range of 0.25 g to 2 g. When the microbicidal composition is applied to the outside surface of the prophylactic device, the amount of microbicidal composition is preferably between about 0.5 g to 2.0 g, more preferably between about 0.75 g to 1.75 g, most preferably between about 1.0 g to 1.5 g. When the microbicidal composition is applied to the inside of the prophylactic device, the amount of microbicidal composition is preferably between about 0.1 g to 1.0 g, more preferably between about 0.15 g to 1.0 g, most preferably between about 0.25 to 0.65 g.

Further features of the present invention will be apparent from the following Examples which are included by way of illustration, not limitation, of the invention.

EXAMPLES

Example 1

Preparation of Microbicidal Composition (3% Active)

TABLE 1

Ingredients for 3% microbicidal composition

| Ingredient | Monograph | Quantity per batch (kg) |
|---|---|---|
| Excipients | | |
| Sodium Hydroxide NF | NF | 0.1443 |
| Edetate Disodium Dihydrate USP | USP | 0.010 |
| Methylparaben NF | NF | 0.018 |
| Propylparaben NF | NF | 0.002 |
| Carbopol 971P NF | NF | 0.500 |
| Propylene Glycol USP | USP | 0.100 |
| Glycerin USP | USP | 0.100 |
| Purified Water I | USP | 1.804 |
| Purified Water II | USP | 8.370 |
| Active Pharmaceutical Ingredients | | |
| SPL7013 | | 0.339 |

Protocol i. The equipment is sanitised and rinsed prior to manufacture.
ii. In a stainless steel jug, Sodium Hydroxide, NF, is dissolved in purified water.
iii. In a stainless steel vessel, Edetate Disodium Dihydrate, USP, is added to purified water and stirred with a high shear mixer until dissolved.
iv. Methyl- and Propyl-paraben, NF, are added one at a time and mixed until fully dispersed.
v. Carbopol 971P, NF, is added slowly and the mixture stirred until the Carbopol 971P, NF, is fully dispersed and a smooth gel is formed.
vi. Propylene glycol, USP, and Glycerin, USP, are added to the vessel and the solution mixed until the contents are fully dispersed.
vii. Sodium Hydroxide solution from Step ii. is added until the pH is 4.5.
viii. Following pH measurement, purified water is added to volume and the solution mixed until all ingredients are dispersed and a homogeneous gel is formed.
ix. The bulk yield is measured.

Example 2

Condom Stability Study 1%, 3% and 5% of Active in Carbopol Gel

Individually packaged male condoms made from natural rubber latex and intended for single use meet with certain minimum requirements specified in ASTM Designation: D 3492-97 (American Society for Testing and Materials, Standard Specification for Rubber Contraceptives, Male Condoms) test method. The test method is designed to ensure that condoms are of consistent quality. Certain ingredients in vaginal formulations may compromise condom integrity. This method was used to determine the effect of vaginal formulations on condoms. The following parameters were determined for the treated and untreated condoms: pressure at burst, volume at burst, length, thickness, and width. If the formulation compromises the condoms, the pressure and volume at burst are expected to be lower. The length of the condoms might be affected as well.

A 4.0 g sample of gel was spread on 7.5 cm×410 cm aluminium foil and wrapped around a condom. The condom was placed on polypropylene dowel and dowel was wrapped with the aluminium foil containing the test article. After 30 min the aluminium foil was removed and the condom was blotted free of adhering gel. The length, width volume, and pressure at burst of the treated condoms were then measured.

Air Burst Properties (Pressure and Volume at Burst)

1. Carry out the test at 25±5° C.
2. Unroll the condom onto the mount without stretching. The length of condom tested should be 150±3 mm (uninflated).
3. Seal the condom to the system with the inflatable rubber ring (this rubber ring clamps off a constant length of the condom).
4. Ensure that air cannot leak through the seal or from the system during inflation.
5. Open the valve controlling the air to the condom and at the same time initiate the chart recorder.
6. Inflate the condom at a constant rate of 0.4 to 0.5 L/s (24 to 30 L/min). Record the flow rate.
7. Pressure is recorded as a function of time until the condom bursts. An immediate rise in the pressure is observed indicating initial time. At burst the pressure returns to zero.
8. Record the bursting pressure (to nearest 0.1 kiloPascals (kPa)) and calculate the bursting volume (to nearest 0.5 L). The pressure at burst can be read from the recording on the chart paper. The volume at burst is calculated using the following equation:

Volume at burst($L$)=Flow rate×time from initiation of study to burst

Data for this experiment is provided in Table 2.

TABLE 2

Exposure of condoms to vaginal gels for 30 minutes.

| | Untreated | | | Treated for 30 Minutes | | | |
|---|---|---|---|---|---|---|---|
| Treatment | Burst pressure (kPa) | Time to Burst (sec) | Burst volume (L) | Burst pressure (kPa) | Time to Burst (sec) | Burst volume (L) | Result |
| Placebo | 1.97 | 84 | 38.27 | 1.96 | 80 | 36.43 | Not compromised |
| 1% gel | 1.97 | 84 | 38.27 | 1.86 | 83 | 37.85 | Not compromised |
| 3% gel | 1.97 | 84 | 38.27 | 1.82 | 82 | 37.58 | Not compromised |
| 5% gel | 1.97 | 84 | 38.27 | 1.91 | 87 | 40.03 | Not compromised |

Measurement of Length

1. Unroll the condom and smooth out the wrinkles (this is not necessary for treated condoms).
2. Put the condom on the mandrel and let it hang freely, stretched only by its own mass.
3. Note, to the nearest millimetre, the length of the condom as indicated on the scale outside the open end of the condom.

Measurement of Width

1. Unroll the condom and smooth out the wrinkles (this is not necessary for treated condoms).
2. Place the condom on a flat surface.
3. Measure to the nearest 0.5 mm the width of the condom laid flat at a distance of 30±5 mm from the open end.

Data from these assays is provided in Table 3.

TABLE 3

Condom dimensions, Burst Strength and Burst Volume after treatment with microbicidal composition

| | | Before Dipping Dimensions (mm) | | After dipping Dimensions (mm) | | Time to Burst (s) | Burst pressure (kPa) | Burst Volume (L) | Average Volume (L) |
|---|---|---|---|---|---|---|---|---|---|
| Condom | Treatment | Length | Width | Length | Width | | | | |
| 1 | Plain (control) | 182 | 53 | | | 85 | 1.98 | 38.99 | 38.27 |
| 2 | Plain (control) | 185 | 53 | | | 83 | 1.9 | 37.93 | |
| 3 | Plain (control) | 184 | 53 | | | 83 | 2.02 | 37.88 | |
| 1 | Placebo gel | 185 | 53 | 187 | 53 | 70 | 1.69 | 32.22 | 36.43 |
| 2 | Placebo gel | 184 | 53 | 186 | 53 | 83 | 2.10 | 37.85 | |
| 3 | Placebo gel | 185 | 53 | 185 | 53 | 86 | 2.09 | 39.23 | |
| 1 | 1% composition | 185 | 53 | 186 | 53 | 83 | 1.9 | 37.93 | 37.85 |
| 2 | 1% composition | 186 | 53 | 185 | 53 | 82 | 1.89 | 37.65 | |
| 3 | 1% composition | 186 | 53 | 184 | 53 | 83 | 1.79 | 37.97 | |
| 1 | 3% composition | 186 | 53 | 187 | 53 | 89 | 1.95 | 40.65 | 37.58 |
| 2 | 3% composition | 187 | 53 | 189 | 53 | 88 | 1.96 | 40.38 | |
| 3 | 3% composition | 186 | 53 | 187 | 53 | 69 | 1.55 | 31.71 | |
| 1 | 5% composition | 185 | 53 | 187 | 53 | 90 | 1.72 | 41.3 | 40.03 |
| 2 | 5% composition | 185 | 53 | 185 | 53 | 82 | 1.9 | 37.65 | |
| 3 | 5% composition | 186 | 53 | 185 | 53 | 80 | 2.1 | 41.14 | |

REFERENCES

1. ASTM Designation: D 3492-97, Standard Specification for Rubber Contraceptives (Male Condoms).

2. Condom Burst Test on a Placebo and Active Gel Formulation, CDDR-R4316-0600-NL-3, Pages 106 of 108 and 107 of 108, Jun. 26, 2000.

Example 3

Evaluation of the Effect of the Microbicidal Composition on Condoms

This investigation assesses the condom strength (using the Burst Test) of condoms lubricated with the microbicidal composition according to the present invention before and after ageing for 7 days at 70° C.

The condoms tested were: DF 53 N Thin, Batch no.: 0509052516 and the tests were conducted in S&T, Shah Alam.

Procedure 1. 0.5 g of the microbicidal composition containing 3% (w/w) of the active was dosed onto the external and internal surfaces of the condom (total: 1.0 g) and sealed in an aluminium foil (56 mm×56 mm);
2. 160 pcs of the condoms were prepared, 80 pcs were kept in an oven at 70° C. for 7 days (aged) for an accelerated shelf life study and the balance 80 pcs were tested without ageing (unaged samples).
3. All of the unaged and aged sample were tested for Burst properties.

Results

Burst Properties (Tested ISO 4074:2002 Standards)

| | Burst Unaged | | | | | | Burst aged (7 days, 70° C.) | | | | | |
|---|---|---|---|---|---|---|---|---|---|---|---|---|
| Batch no. | MV | SDV | NCV | MP | SDP | NCP | MV | SDV | NCV | MP | SDP | NCP |
| 0509052516 | 51.34 | 5.93 | 0 | 1.63 | 0.18 | 2 | 44.14 | 3.01 | 0 | 1.49 | 0.10 | 0 |

Remarks:
MV—Mean volume,
SDV—Standard deviation of volume,
NCV—Non-compliance of volume,
MP—Mean pressure,
SDP—Standard deviation of pressure,
NCP—Non-compliance of pressure Results of the Burst Test showed that the microbicidal composition containing 3% (w/w) of the active has caused a significant drop in the mean volumes and pressure by 14.0% and 8.6% respectively but both mean volumes and pressures were well above the accepted criteria (Burst volume: 18 litres, Burst pressure: 1 kPa) Therefore, we conclude that even though the microbicidal composition containing 3% (w/w) of the active has significantly reduced the burst volume and pressure of the condom (DF 53 Thin) the effect is still acceptable.

Example 4

Migration Test for the Microbicidal Composition Containing 3% (w/w) of the Active

| Sample: | Bulk condom DF 53N Thin, the microbicidal composition containing 3% (w/w) of the active |
|---|---|
| Dosing: | 1. 0.5 g internal & external condom |
| | 2. 0.5 g external only |

Results

Condoms were prepared according to Example 3 above, and were kept at room temperature and tested for lubricant migration every week for 7 weeks. The condoms were unrolled carefully and placed on a piece of clean paper. The distance traveled by the lubricant from the teat of the condom was measured by a ruler.

| Date | Ageing time/ weeks | Samples | Dosing internal & external | | | Dosing external only | | |
|---|---|---|---|---|---|---|---|---|
| | | | 1 | 2 | mean | 1 | 2 | mean |
| 6-Oct-05 | 0 (24 hours) | 1 | 2.50 | 4.00 | 3.25 | 3.50 | 2.00 | 2.75 |
| | | 2 | 2.80 | 3.60 | 3.20 | 2.00 | 1.90 | 1.95 |
| | | | | | 3.23 | | | 2.35 |
| 13-Oct-05 | 1 | 1 | 3.40 | 4.00 | 3.70 | 0.90 | 2.50 | 1.70 |
| | | 2 | 2.10 | 2.00 | 2.05 | 2.50 | 1.20 | 1.85 |
| | | | | | 2.88 | | | 1.78 |
| 20-Oct-05 | 2 | 1 | 3.90 | 2.00 | 2.95 | 2.70 | 2.70 | 2.70 |
| | | 2 | 1.70 | 4.00 | 2.05 | 2.80 | 2.80 | 2.55 |
| | | | | | 2.50 | | | 2.63 |
| 27-Oct-05 | 3 | 1 | 2.40 | 3.50 | 2.45 | 2.70 | 2.20 | 2.45 |
| | | 2 | 2.70 | 3.20 | 2.95 | 2.50 | 2.50 | 2.50 |
| | | | | | 2.70 | | | 2.48 |
| 3-Nov-05 | 4 | 1 | — | — | — | — | — | — |
| | | 2 | — | — | — | — | — | — |
| 10-Nov-05 | 5 | 1 | 3.90 | 3.30 | 3.60 | 2.30 | 2.10 | 2.20 |
| | | 2 | 3.20 | 2.90 | 3.05 | 2.60 | 3.10 | 2.85 |
| | | | | | 3.33 | | | 2.53 |
| 17-Nov-05 | 6 | 1 | 3.10 | 3.30 | 3.20 | 3.20 | 2.70 | 2.95 |
| | | 2 | 2.00 | 2.50 | 2.25 | 1.90 | 2.40 | 2.15 |
| | | | | | 2.73 | | | 2.55 |
| 24-Nov-05 | 7 | 1 | 2.80 | 4.80 | 3.80 | 2.90 | 3.00 | 2.95 |
| | | 2 | 3.90 | 2.80 | 3.35 | 1.50 | 1.70 | 1.60 |
| | | | | | 3.58 | | | 2.28 |

Example 5

Study to Assess the Effect of the Microbicidal Composition According to the Present Invention on HSV-2 Susceptibility

BACKGROUND

The study was conducted to detect potential adverse effects of the microbicidal composition according to the present invention by measuring susceptibility of mice to infection with herpes simplex virus type 2 (HSV-2), the virus that most commonly causes genital herpes.

The mouse HSV-2 vaginal transmission model is used by Richard Cone at Johns Hopkins University, Baltimore, USA, to assess toxicities associated with microbicides that could lead to susceptibility to pathogens such as HSV-2.

Methods

Mouse Model:

Prior to the susceptibility assessment, female CF-1 mice (Harlan, Indianapolis, Ind., USA) 6-8 weeks old are progestin treated (Depo Provera®, medroxyprogesterone acetate) to increase HSV-2 susceptibility, and to make the mice more uniform in terms of susceptibility than mice at different stages of the oestrous cycle.

Viral Inoculum:

Strain G of HSV-2, $5 \times 10^8$ $TCID_{50}$/mL.

Procedures:

20 µL of the microbicidal composition according to the present invention was administered to the vagina followed 12 hours later by administration of a low-dose inoculum of HSV-2 (0.1 $ID_{50}$) delivered in 10 µL of Bartels medium. Control animals received 20 µL of PBS instead of test product.

The inoculum is delivered 12 hours after application of the test product because previous experiments showed that this was the time at which peak susceptibility to HSV-2 infection occurred following administration of nonoxynol-9.

In this study, a total of 40 mice received the microbicidal composition according to the present invention and a total of 40 mice received PBS.

Results

Only 1 out of the 40 mice treated with the microbicidal composition according to the present invention became infected with HSV-2. In contrast, 7 out of 40 mice in the control group became infected. In other words, there was no increase in susceptibility following administration of the microbicidal composition according to the present invention.

In previous studies, 29 out of 42 animals treated with nonoxynol-9, 20 out of 30 animals treated with microbicide ingredient 1, and 25 out of 41 animals treated with microbicide ingredient 2, became infected.

To determine relative susceptibility of the mice in previous studies, two groups of control mice were treated with PBS for every group of mice treated with test product. One control group was inoculated with $0.1\ ID_{50}$, while the other was inoculated with $10\ ID_{50}$. The fraction of animals infected in each control group was then used to construct a dose-response graph (fraction infected vs. log ID), drawing a linear interpolation between the low and high dose points. The fraction of mice infected in the test group was then plotted on this graph to determine the effective ID of the low-dose inoculum in this test group. Relative susceptibility was defined as the effective ID the low-dose inoculum delivered to the test mice divided by the ID it delivered to the control animals.

Animals treated with nonoxynol-9 were 29.7 times more susceptible to HSV-2 infection than the control animals ($P<0.001$, Fishers exact two-sided t-test), while animals treated with microbicide ingredients 1 and 2 were 29.1 ($P<0.001$) and 17.5 ($P<0.001$) times more susceptible, respectively.

Conclusion

The microbicidal composition according to the present invention does not appear to lead to increased susceptibility in the mouse-model of HSV-2 infection. Nonoxynol-9 and other detergent microbicides may lead to increased susceptibility.

Reference

Cone R A, Hoen T E, Wang X X & Moench T R. Microbicidal Detergents Increase HSV Susceptibility in Mice Without Causing Visible Epithelial Defects. Abstract # 02421, "Microbicides 2004" Conference, London, UK; March 2004.

It will be appreciated that variations and modifications may be made to the invention as broadly described herein, other than those specifically described without departing from the spirit and scope of the invention. It is to be understood that this invention extends to include all such variations and modifications.

The claims defining the invention are as follows:

1. A microbicidal delivery system comprising a microbicidal composition comprising compound of formula I

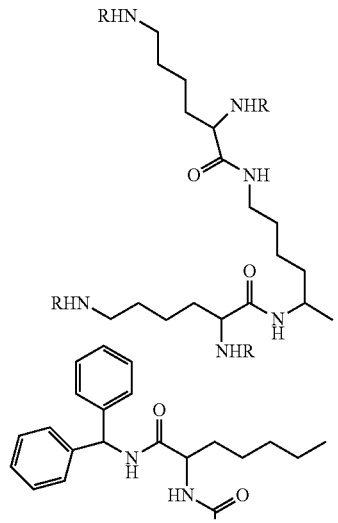

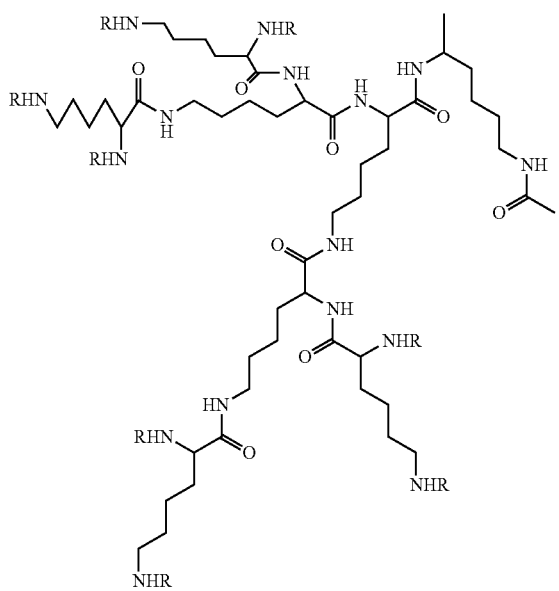

-continued

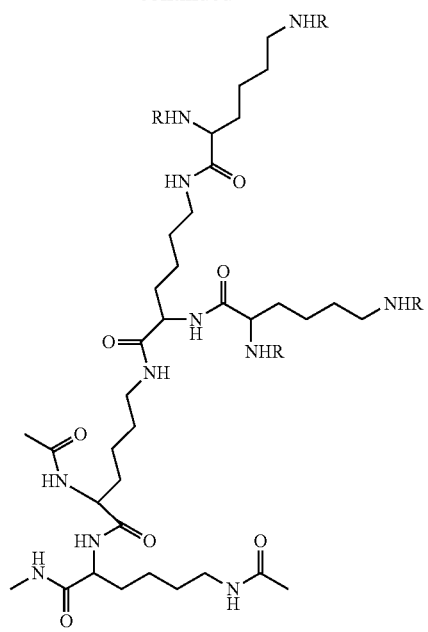

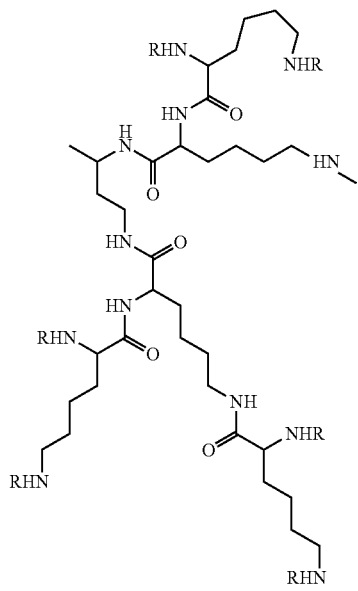

-continued

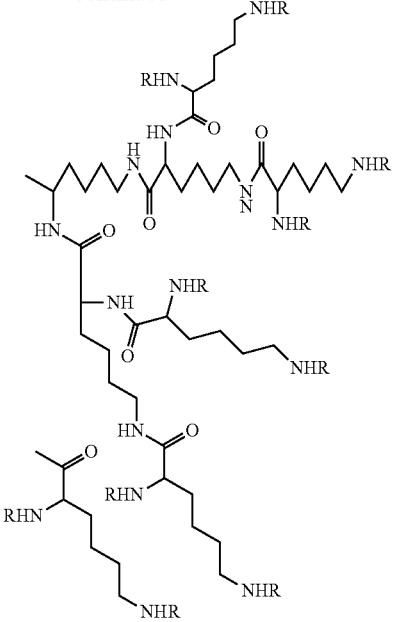

where R represents a group of the formula IV $$IV$$

or a pharmaceutically acceptable salt or solvate thereof;
a carrier, excipient or diluent therefor; and
a prophylactic device selected from the group consisting of a condom, cervical cap, contraceptive diaphragm, and vaginal sponge;
the microbicidal composition being carried on a surface of the prophylactic device, and being compatible therewith.

2. A microbicidal delivery system according to claim 1, wherein the microbicidal composition is carried on an external surface, and/or an internal surface of the prophylactic device.

3. A microbicidal delivery system according to claim 2, wherein the microbicidal composition covers at least a substantial portion of the external surface and/or the internal surface of the prophylactic device.

4. A microbicidal delivery system according to claim 1 wherein the prophylactic device comprises latex.

5. A microbicidal delivery system according to claim 1, wherein the prophylactic device is a condom.

6. A microbicidal delivery system according to claim 1, wherein the compound is a metallic salt selected from the group consisting of one or more of aluminium, calcium, lithium, magnesium, potassium, sodium and zinc salts.

7. A microbicidal delivery system according to claim 1, wherein the compound is an organic salt selected from the group consisting of one or more of N,N'-dibenzylethylenediamine, chloroprocaine, diethanolamine, ethylenediamine, cyclohexylamine, meglumine (N-methylglucamine) and procaine.

8. A microbicidal delivery system according to claim 1, wherein the compound is selected from one or more of the group consisting of one or more of a quaternary amine, a sulphonium salt and phosphonium salt.

9. A microbicidal delivery system according to claim 1, wherein the carrier, excipient or diluent includes one or more of the group consisting of sodium hydroxide, water soluble oils, buffering agents, propylene glycol, glycerine, methyl paraben, propyl paraben, disodium edetate dihydrate and water.

10. A microbicidal delivery system according to claim 1, wherein the microbicidal composition further includes a secondary pharmaceutically active compound which is a contraceptive or an agent active against sexually transmitted infections.

11. A microbicidal delivery system according to claim 10, wherein the secondary pharmaceutically active compound is a contraceptive.

12. A microbicidal delivery system according to claim 11, wherein the secondary pharmaceutically active compound is a spermicide.

13. A microbicidal delivery system according to claim 10, wherein the secondary pharmaceutically active compound is selected from one or more of the group consisting of podophyllin, tetracycline, nystatin, fluconazole, metronidazole, acyclovir, penicillin, cefotaxime, specinomycin, retrovir, erythromycin, ceftriaxone, cotrimoxazole, cotrimoxazole, benzyl benzoate, nonoxynol-9, octoxynol-9, menfegol, progestin, estrogen and estradiol.

14. A microbicidal delivery system according to claim 1, wherein the microbicidal compound is present in the microbicidal composition in an amount of from about 0.5% to 20% weight/weight.

15. A microbicidal delivery system according to claim 14 wherein the microbicidal compound is present in the microbicidal composition in an amount of from about 2% to 15% weight/weight.

16. A microbicidal delivery system according to claim 1, wherein the microbicidal composition is present in an amount of from about 0.25 to 2 g.

17. A microbicidal delivery system according to claim 1 wherein the microbicidal composition is present in an amount of 0.1 g to 1 g.

* * * * *

UNITED STATES PATENT AND TRADEMARK OFFICE
CERTIFICATE OF CORRECTION

PATENT NO. : 8,568,753 B2  
APPLICATION NO. : 12/090580  
DATED : October 29, 2013  
INVENTOR(S) : Grogan et al.

Page 1 of 8

It is certified that error appears in the above-identified patent and that said Letters Patent is hereby corrected as shown below:

In the Specification

In columns 1-2 lines 40-60,

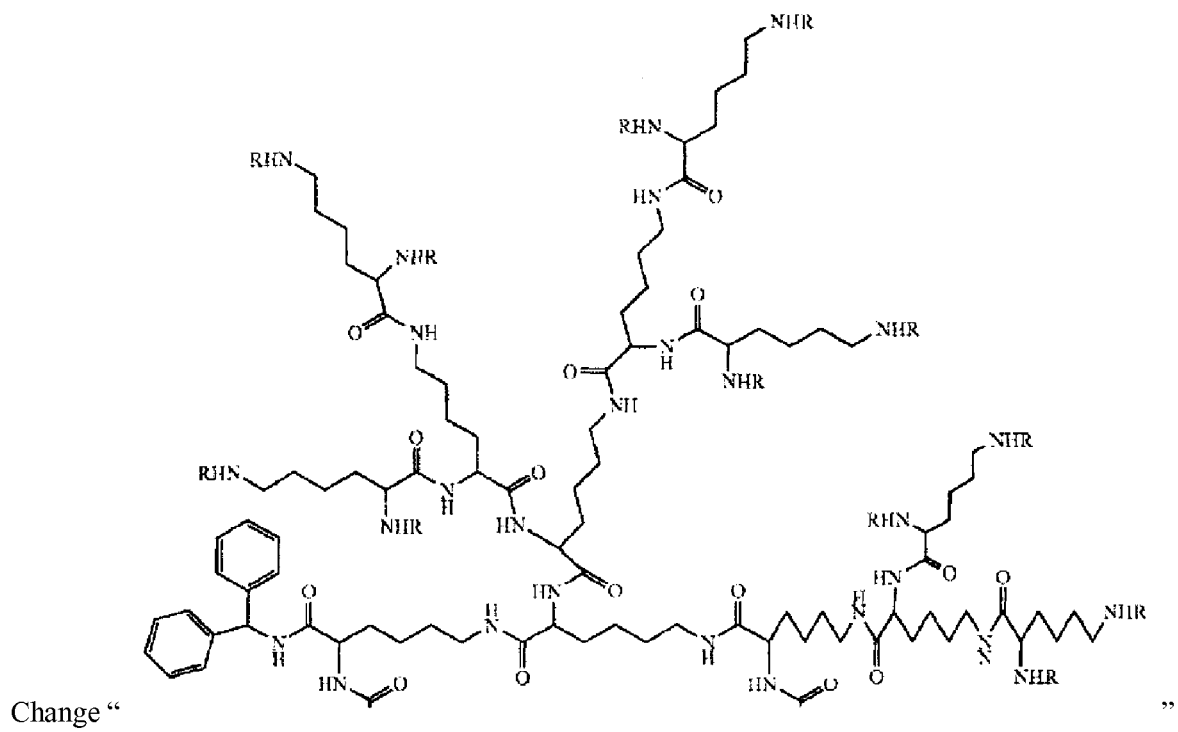

Change " "

Signed and Sealed this  
Fifth Day of August, 2014

Michelle K. Lee  
*Deputy Director of the United States Patent and Trademark Office*

CERTIFICATE OF CORRECTION (continued)
U.S. Pat. No. 8,568,753 B2

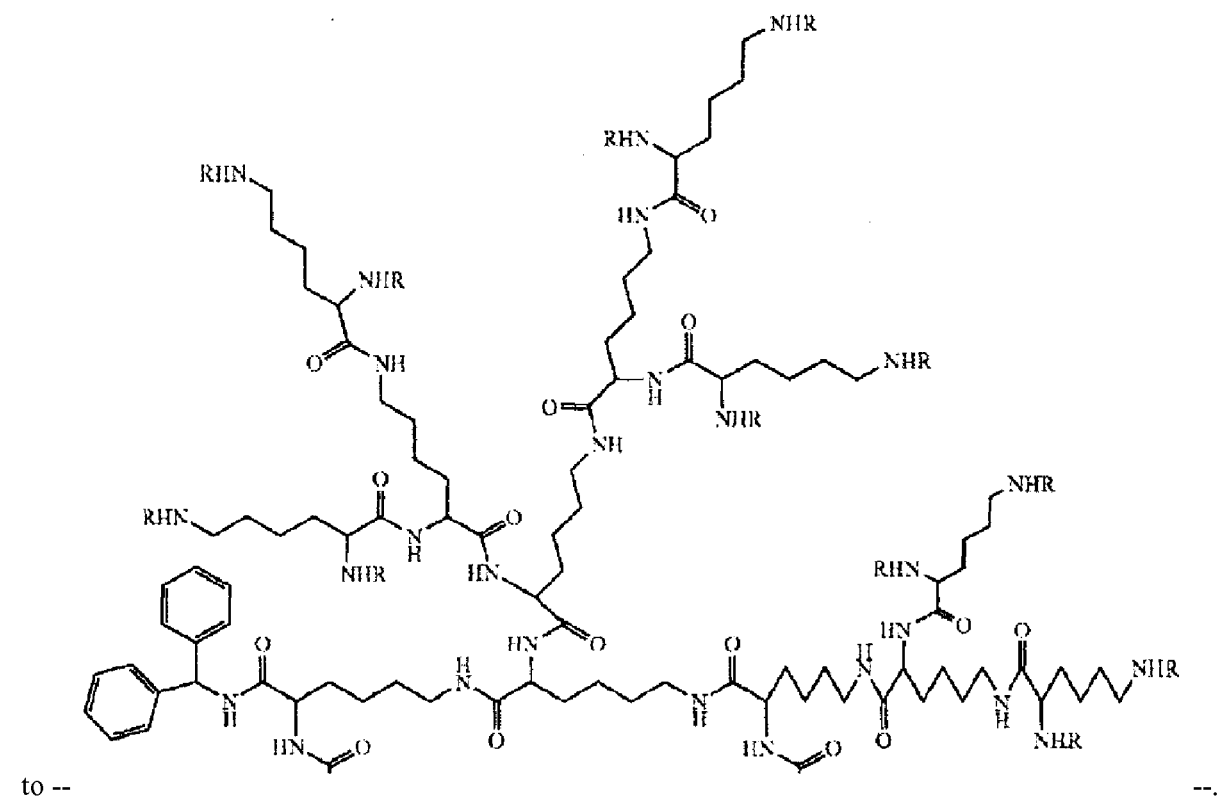

to --                                                                                           --.

In columns 5-6 lines 37-60,

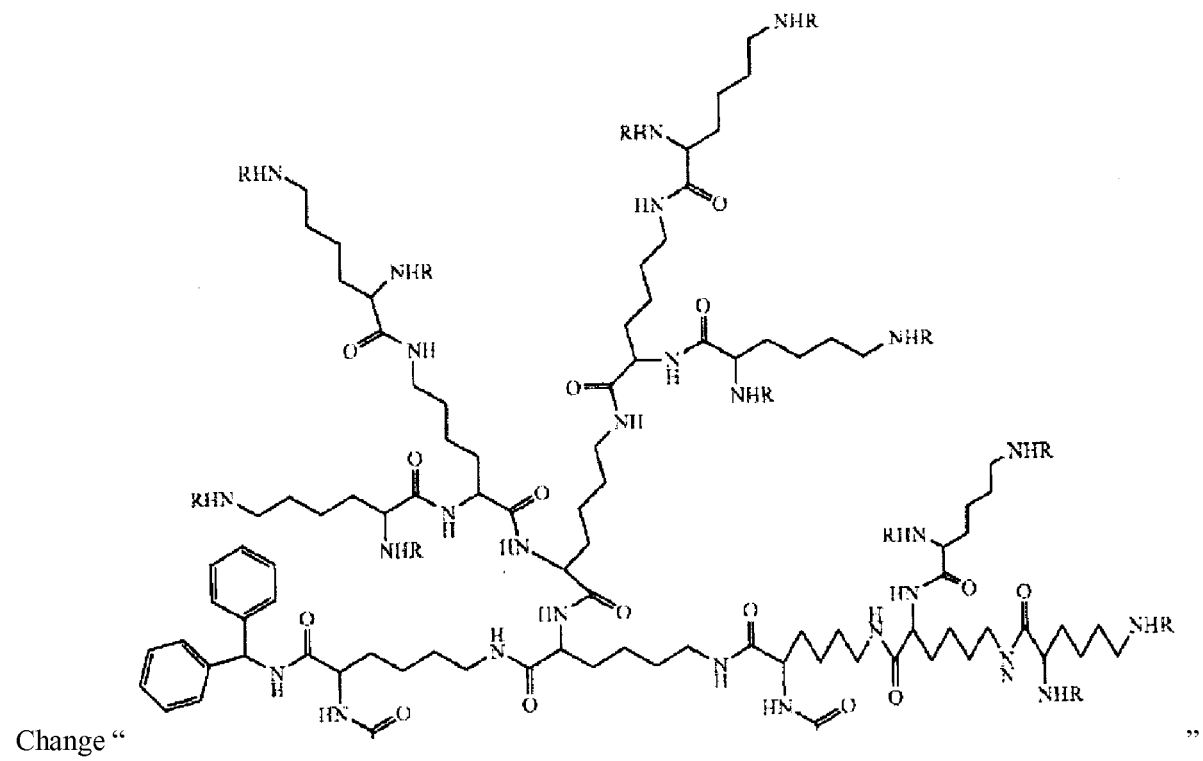

Change "                                                                                       "

CERTIFICATE OF CORRECTION (continued)
U.S. Pat. No. 8,568,753 B2 to --
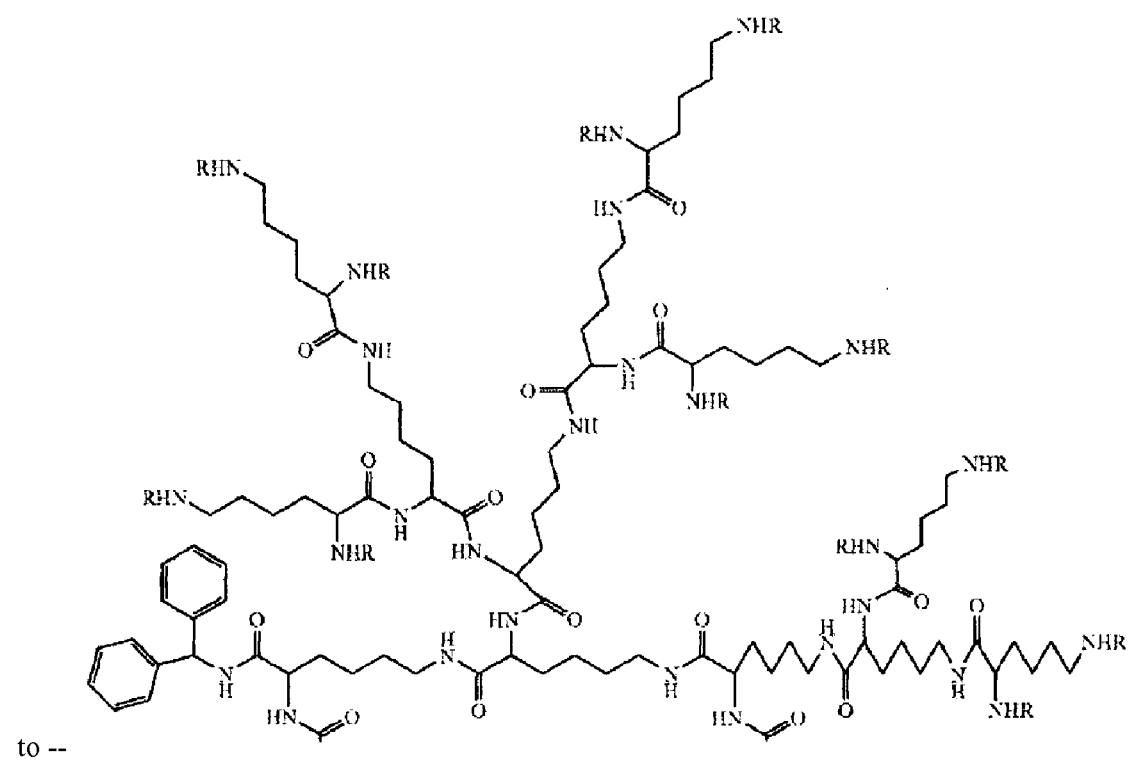
--.

In columns 11-12 lines 1-28,

Change "
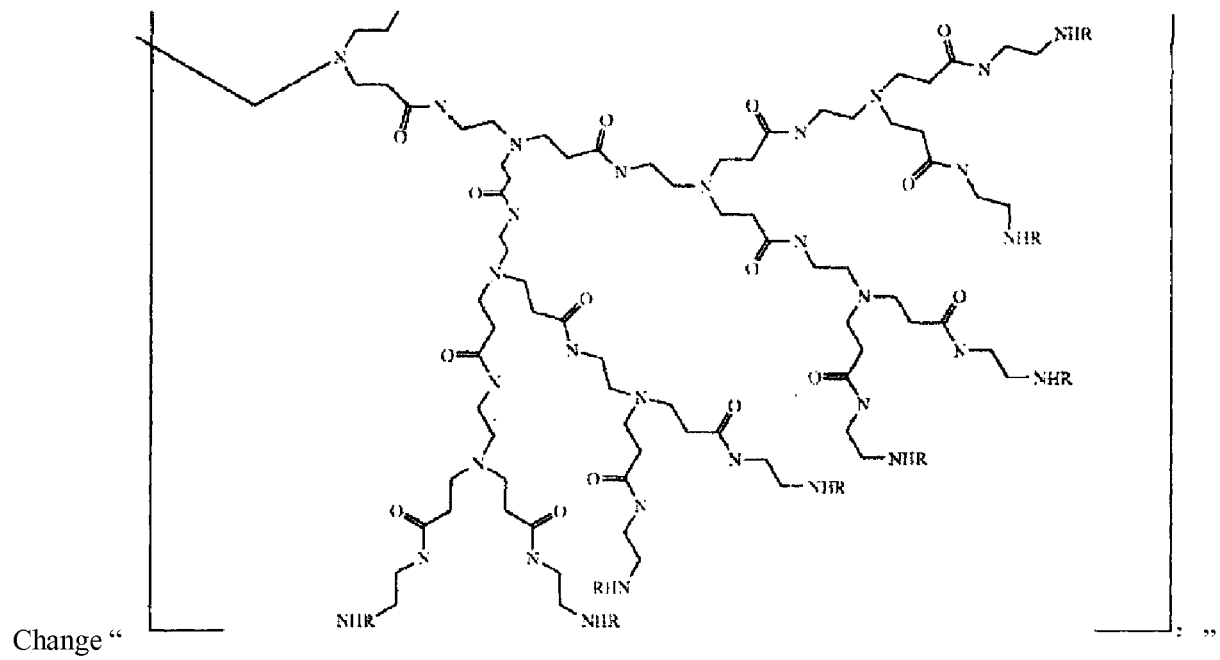
; "

to -- 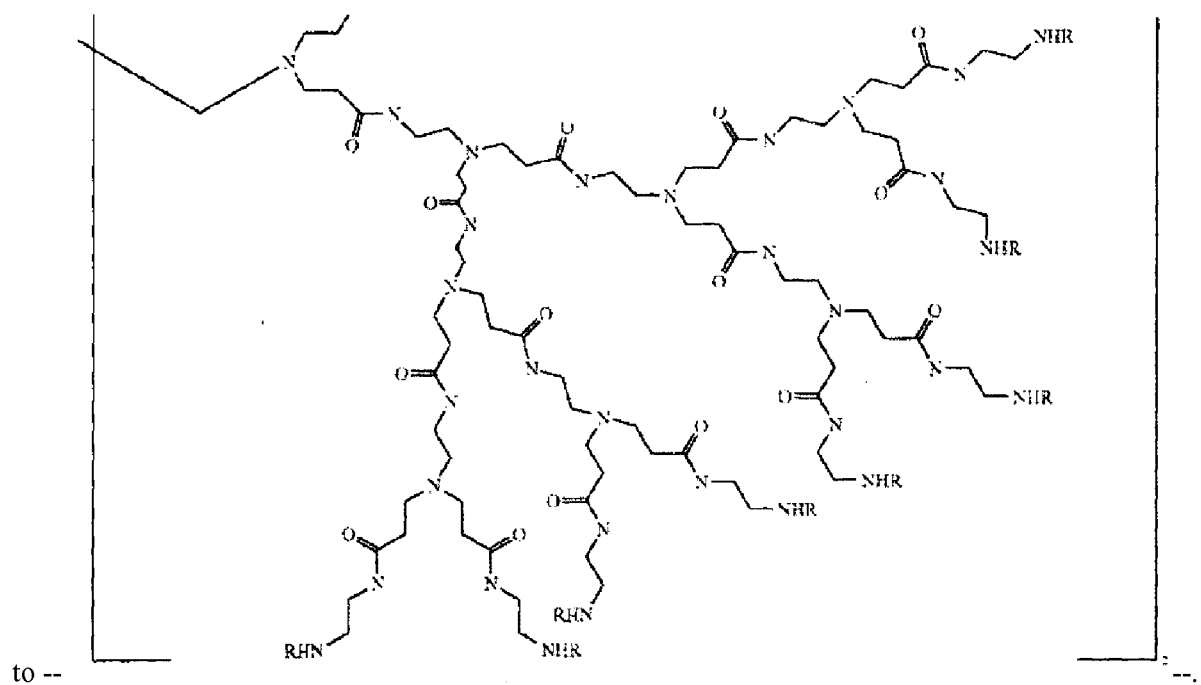 --.
In column 12 line 55, Change "N,N¹" to --N,N'--.
In column 14 line 38, Change "nyastatin," to --nystatin,--.
In column 14 line 55, Change "type." to --type:--.

CERTIFICATE OF CORRECTION (continued)
U.S. Pat. No. 8,568,753 B2

Page 5 of 8

In columns 15-16 lines 5-60,

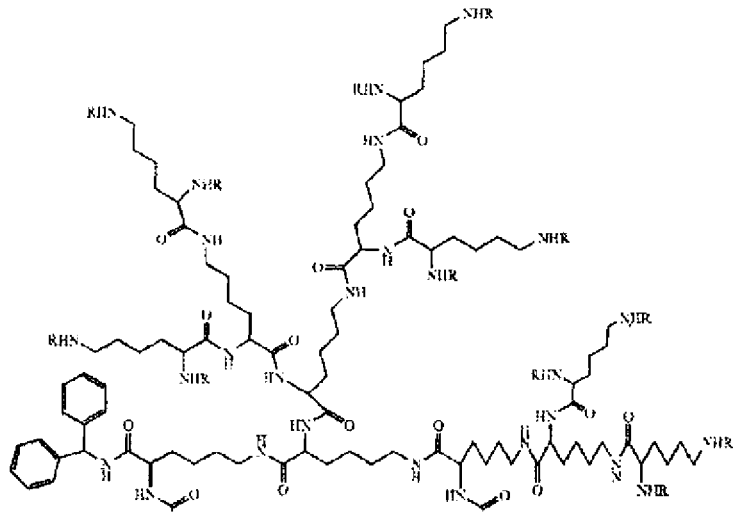

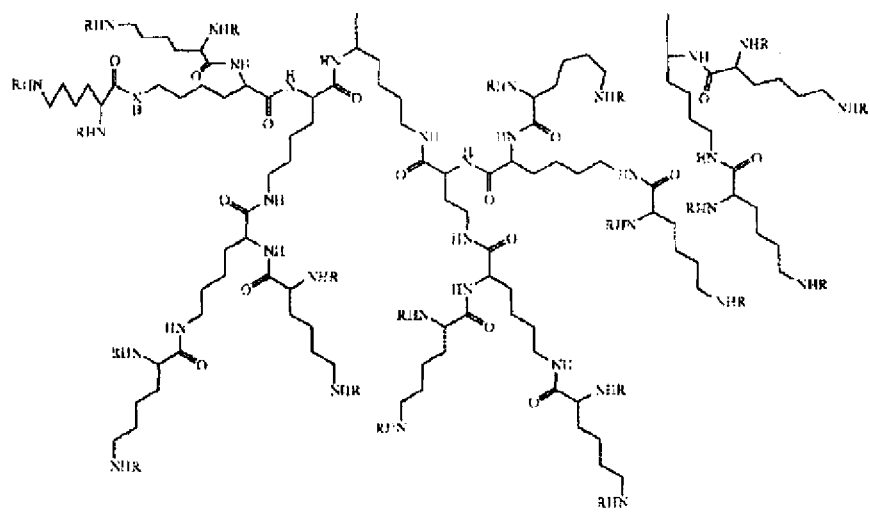

Change " "

CERTIFICATE OF CORRECTION (continued)
U.S. Pat. No. 8,568,753 B2 to --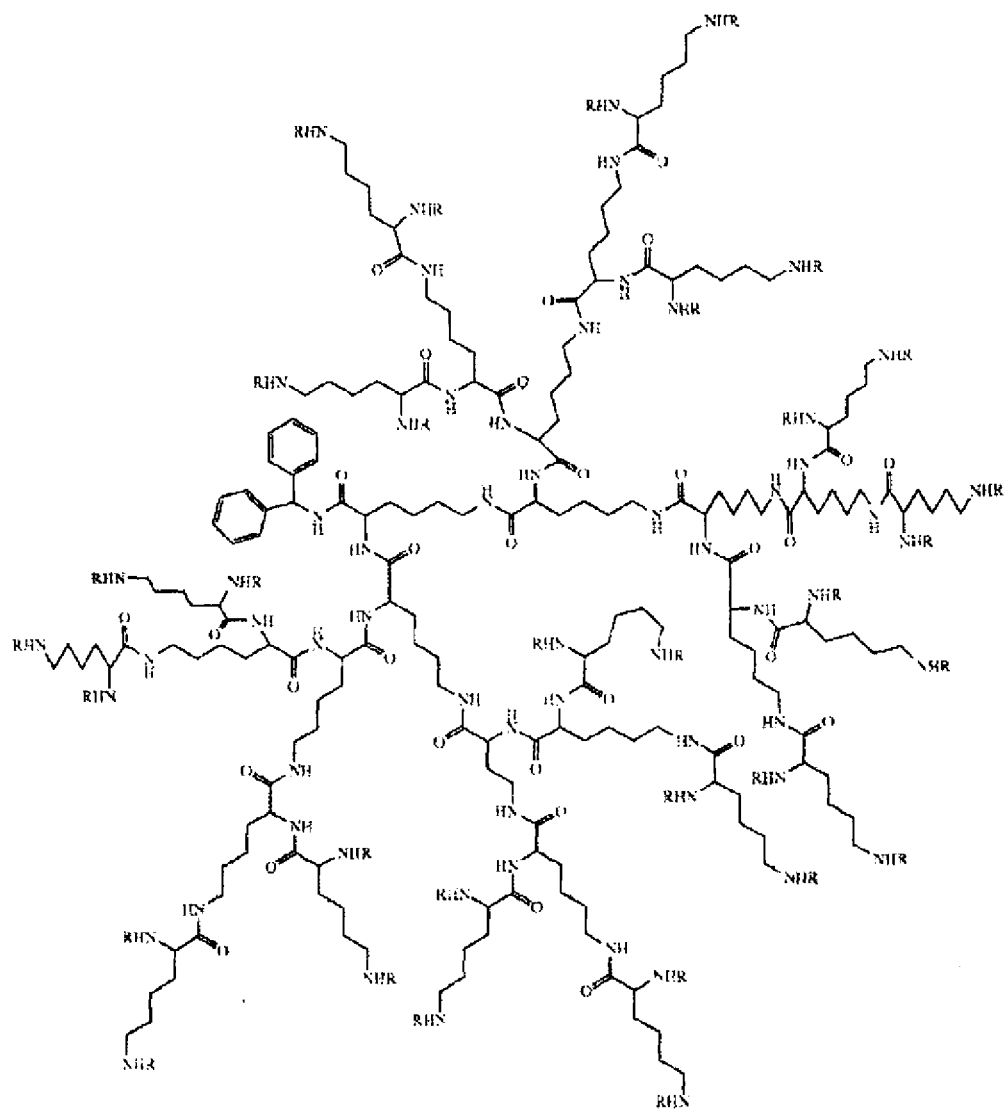--.

In column 22 line 16, Change "mm);" to --mm).--.

In the Claims

In column 26 line 4, In Claim 1, Change "comprising" to --comprising a--.

CERTIFICATE OF CORRECTION (continued)
U.S. Pat. No. 8,568,753 B2

In column 28 lines 1-25,

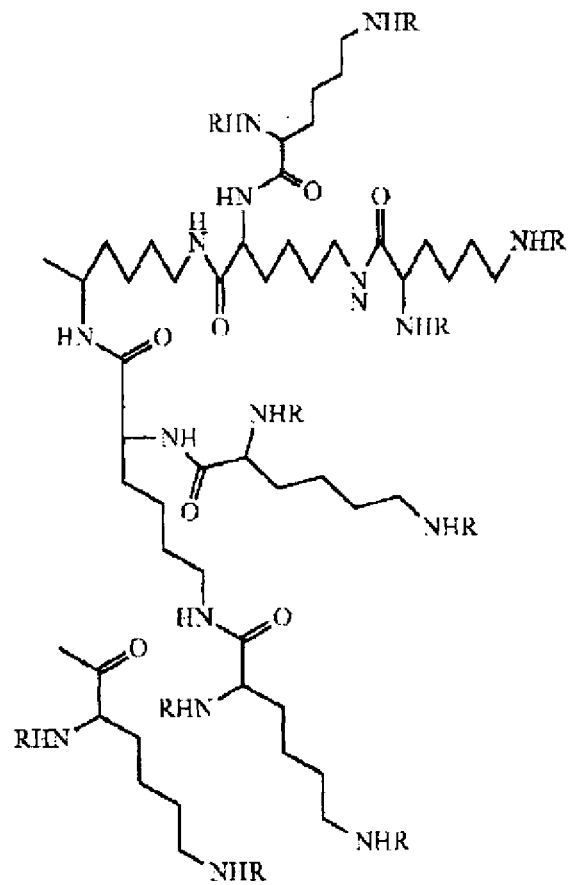

Change "                                                                                     "

CERTIFICATE OF CORRECTION (continued)
U.S. Pat. No. 8,568,753 B2 to --

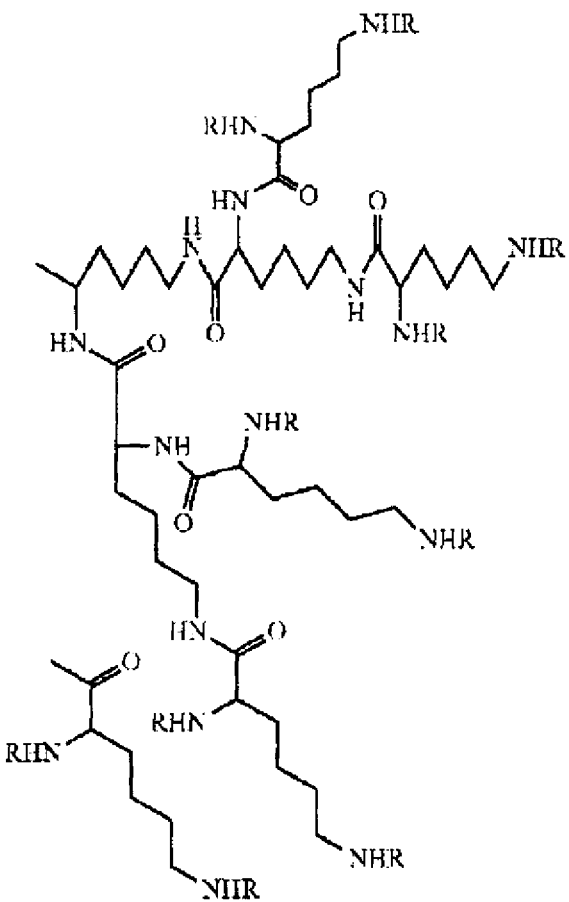

--.

In column 30 line 8, In Claim 13, Change "specinomycin," to --spectinomycin,--.

In column 30 line 9, In Claim 13, Change "cotrimoxazole, cotrimoxazole," to --cotrimoxazole,--.

In column 30 line 11, In Claim 14, Change "claim l," to --claim 1,--.

UNITED STATES PATENT AND TRADEMARK OFFICE
CERTIFICATE OF CORRECTION

PATENT NO. : 8,568,753 B2
APPLICATION NO. : 12/090580
DATED : October 29, 2013
INVENTOR(S) : Grogan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 975 days.

Signed and Sealed this
Nineteenth Day of May, 2015

Michelle K. Lee
*Director of the United States Patent and Trademark Office*